United States Patent
Shen et al.

(10) Patent No.: US 12,279,777 B2
(45) Date of Patent: Apr. 22, 2025

(54) DETACHABLE TITANIUM CLIP ASSEMBLY AND USE METHOD

(71) Applicant: Jiongchao Shen, Shenzhen (CN)

(72) Inventors: Jiongchao Shen, Shenzhen (CN); Guoxi Yang, Shenzhen (CN); Yelin Shen, Shenzhen (CN)

(73) Assignee: Jiongchao Shen, Shenzhen (CN)

( * ) Notice: Subject to any disclaimer, the term of this patent is extended or adjusted under 35 U.S.C. 154(b) by 0 days.

(21) Appl. No.: 18/650,354

(22) Filed: Apr. 30, 2024

(65) Prior Publication Data

US 2024/0277344 A1   Aug. 22, 2024

(30) Foreign Application Priority Data

Dec. 6, 2023   (CN) .......................... 202311663575.7

(51) Int. Cl.
*A61B 17/122* (2006.01)
*A61B 17/12* (2006.01)
*A61B 17/128* (2006.01)

(52) U.S. Cl.
CPC ........ *A61B 17/122* (2013.01); *A61B 17/1285* (2013.01); *A61B 2017/12004* (2013.01)

(58) Field of Classification Search
None
See application file for complete search history.

(56) References Cited

U.S. PATENT DOCUMENTS

| 4,765,335 | A | * | 8/1988 | Schmidt ............. A61B 17/1227 24/552 |
| 5,084,057 | A | * | 1/1992 | Green ................ A61B 17/1285 227/19 |
| 5,395,381 | A | * | 3/1995 | Green ....................... F16B 2/22 227/19 |
| 8,066,722 | B2 | * | 11/2011 | Miyagi .............. A61B 17/1285 606/142 |
| 2003/0171759 | A1 | | 9/2003 | Sadler et al. |
| 2007/0198032 | A1 | * | 8/2007 | Ortiz .................... A61B 17/128 606/138 |
| 2010/0274267 | A1 | | 10/2010 | Rothstein |
| 2014/0343581 | A1 | | 11/2014 | Lee |
| 2018/0078261 | A1 | * | 3/2018 | King ...................... A61B 17/10 |
| 2018/0271535 | A1 | * | 9/2018 | Shellenberger .... A61B 17/1285 |
| 2019/0231353 | A1 | * | 8/2019 | Saenz Villalobos ........................ A61B 17/122 |
| 2020/0008811 | A1 | * | 1/2020 | Itoh .................... A61B 17/1285 |
| 2020/0100791 | A1 | * | 4/2020 | Tsuchiya .............. A61B 17/122 |
| 2020/0214705 | A1 | * | 7/2020 | Yuasa .................. A61B 17/122 |
| 2020/0222055 | A1 | * | 7/2020 | Ibrahim ................ A61M 39/10 |

(Continued)

Primary Examiner — Shaun L David

(57) ABSTRACT

The invention discloses a detachable titanium clip assembly and a use method. The detachable titanium clip assembly comprises a titanium clip body, wherein the titanium clip body comprises first clip arms, one ends of elastically deformable connecting rods are arranged at tails of the first clip arms, the other ends of the connecting rods are integrated to form a connecting end, and a fragile portion is arranged at the connecting end; a sleeve, wherein the sleeve is disposed around the titanium clip body, the titanium clip body is forced to be closed by pushing the sleeve on the titanium clip body, and a circular step is arranged on a side face of the sleeve; a clip implanting device for implanting the titanium clip body; and a clip withdrawing device for detaching the titanium clip body.

8 Claims, 5 Drawing Sheets

(56) References Cited

U.S. PATENT DOCUMENTS

| | | | |
|---|---|---|---|
| 2021/0290240 A1* | 9/2021 | Yoshii | A61B 17/1285 |
| 2021/0298758 A1* | 9/2021 | Thomas | A61B 17/1222 |
| 2021/0380614 A1* | 12/2021 | Koura | C12P 13/001 |
| 2022/0354484 A1* | 11/2022 | Boyers | A61B 17/1285 |
| 2023/0071943 A1* | 3/2023 | Pic | A61B 17/1285 |
| 2023/0181195 A1* | 6/2023 | Singh | A61B 17/10 606/142 |
| 2023/0248370 A1* | 8/2023 | Ortiz Garcia | A61B 17/122 606/156 |
| 2023/0346386 A1* | 11/2023 | Zhang | A61B 17/10 |

* cited by examiner

DETACHABLE TITANIUM CLIP ASSEMBLY AND USE METHOD

BACKGROUND OF THE INVENTION

Technical Field

The invention relates to the technical field of medical instruments, in particular to a detachable titanium clip assembly and a use method.

Description of Related Art

With the development of endoscopic surgery, hemostatic tools are increasingly diversified, and titanium clips are the most common hemostatic tools. The titanium clip typically comprises a V-shaped clip body made from a pure titanium wire or a titanium alloy wire by pressing, and horizontal grooves are formed in inner sides of clipping sections of the clip body to clip tissues. The titanium clips are mainly used for wound suture and hemostasis.

Although the titanium clip is made from medical metal materials that can be left in human bodies, the dwell of the titanium clip in human bodies will cause discomfort of some sensitive patients. The dwell of the titanium clip in some sensitive parts such as the mouth and upper section of the oesophagus, the throat and sphincter ani will lead to an intense abnormal sensation of patients; in addition, because mucosa of these parts is highly active, the tail of the titanium clip may scratch the mucosa on the opposite side, leading to bleeding and infection, so many clinical patients desire to remove the titanium clip after surgery. All titanium clips on the present market are undetachable, or are difficult to remove or are removed by pulling, which often results in direct damage to human tissues and secondary injuries to operative wounds, leading to unsatisfactory clinic application of titanium clips.

BRIEF SUMMARY OF THE INVENTION

In view of the defects existing in the prior art, the objective of the invention is to provide a detachable titanium clip assembly and a use method.

To fulfill the above objective, the invention adopts the following technical solution:

A detachable titanium clip assembly comprises:

a titanium clip body, wherein the titanium clip body comprises two first clip arms, a hinge bar is arranged between the first clip arms, the first clip arms are allowed to move along the hinge bar to be opened or closed, one ends of elastically deformable connecting rods are arranged at tails of the first clip arms, the other ends of the connecting rods are integrated to form a connecting end, and a fragile portion to be snapped under an external force is arranged at the connecting end;

a sleeve, wherein the sleeve is cylindrical and disposed around the titanium clip body, the first clip arms of the titanium clip body are forced to be closed by pushing the sleeve on the titanium clip body, a circular step protruding outwards is arranged on a side face of the sleeve, sliding grooves are formed in an inner wall of the sleeve, and two ends of the hinge bar are arranged in the sliding grooves; wherein, limiting portions for preventing the titanium clip body from being further pulled upwards are arranged at top ends of the sliding grooves or in the sleeve;

a clip implanting device, wherein the clip implanting device comprises a clip implanting sheath and a clip implanting handle, an end of the clip implanting sheath abuts against the sleeve, a first pull wire is arranged in the clip implanting sheath, a first clipping portion to be held or gripped by fingers is arranged on the clip implanting handle, a first moving portion to be held or gripped by fingers is disposed around the clip implanting handle, one end of the first pull wire is connected to the first moving portion, the other end of the first pull wire is connected to the fragile portion, and the first moving portion is vertically pushable with respect to the clip implanting handle to drive the titanium clip body to move vertically in the sleeve; and a clip withdrawing device, wherein the clip withdrawing device comprises a clip withdrawing sheath and a clip withdrawing handle, a rotary sleeve is rotatably mounted at one end of the clip withdrawing sheath, the other end of the clip withdrawing sheath is connected to the clip withdrawing handle, the rotary sleeve is hinged and connected to two second clip arms used for clipping, one end of each of the second clip arms is formed with a jaw and located outside the rotary sleeve, the other end of each of the second clip arms is connected to a second pull wire, a second clipping portion to be held or gripped by fingers is arranged on the clip withdrawing handle, a second moving portion to be held or gripped by fingers is disposed around the clip withdrawing handle, the second pull wire is connected to the second moving portion, the second moving portion is vertically pushable with respect to the clip withdrawing handle, a push ring is arranged on the clip withdrawing handle and connected to a metal bar, receding holes are formed in positions, corresponding to the metal bar, of the second clip arms, the metal bar penetrates through the clip withdrawing handle to be arranged in the clip withdrawing sheath and abuts against the connecting end of the titanium clip body after being pushed forwards by the push ring, and the second clip arms are able to clip the circular step on the sleeve to prevent the sleeve from moving.

Preferably, a cross-section of the circular step is frustum-shaped, an area of a bottom of the circular step is greater than an area of a top of the circular step, and a maximum diameter of the circular step is less than 3.6 mm.

Preferably, the circular step is replaced with a circular groove or a hollow groove.

Preferably, a top surface of the connecting end of the titanium clip body is a flat surface.

Preferably, circular rings allowing fingers to penetrate through are arranged on the first clipping portion, the first moving portion, the second clipping portion and the second moving portion.

Preferably, the clip implanting sheath and the clip withdrawing sheath are both flexible sheaths.

Preferably, hooks are arranged at mouths of the first clip arms and the second clip arms respectively.

Preferably, a flat plate is arranged at a top end of the metal bar.

A use method of the detachable titanium clip assembly comprises the following steps:

S1, in a default state where the clip implanting device, the titanium clip body and the sleeve are assembled together and the titanium clip body is in a closed state, operating the clip withdrawing device, and keeping the first moving portion of the clip withdrawing device static for later use;

S2, inserting the clip implanting device into a human body along an endoscope; when the clip implanting device is pushed to a soft tissue, that is, the first clip arms of the titanium clip body reach the soft tissue, operating the clip implanting handle of the clip implanting device to push the first moving portion forwards to gradually push the first clip arms out of the sleeve to be opened, then pushing the first clip arms in the open state to the soft tissue, then pushing the first moving portion backwards to pull the connecting end of the titanium clip body by means of the first pull wire such that the titanium clip body is gradually pulled back into the sleeve, and in the process of gradually pulling the titanium clip body back into the sleeve, gradually closing the first clip arms of the titanium clip body until the soft tissue is clipped by the first clip arms;

S3, after the titanium clip body clips the soft tissue, because the titanium clip body will not be pulled by further pulling the first pull wire under the action of the limiting portions, applying a greater force to the first moving portion to snap the fragile portion of the first pull wire;

S4, after the first pull wire is snapped, disconnecting the clip implanting device from the titanium clip body and the sleeve, then taking the clip implanting device out of the endoscope, and at this moment, still clipping the soft tissue by the titanium clip body under the action of the sleeve;

S5, when the titanium clip body needs to be detached, pushing the endoscope to the titanium clip body, and then inserting the clip withdrawing device into the human body along the endoscope, wherein the push ring is maintained at an outmost end and the metal bar is maintained in the receding holes;

S6, placing the second clip arms of the clip withdrawing device on the circular step on the sleeve, then pushing the second moving portion forwards to drive the second clip arms to be opened and abut against the circular step, then pushing the second moving portion reversely to drive the second clip arms to clip the circular step, and then keeping the second moving portion static; and S7, after the second clip arms clip the circular step, pushing the push ring forwards with an external force to gradually push the metal bar out of the receding holes to abut against the connecting end of the titanium clip body, then further pushing the push ring to push the titanium clip body out of the sleeve to release the soft tissue, and at this moment, taking the titanium clip body and the sleeve out of the human body by means of the second clip arms of the clip withdrawing device.

By adopting the above technical solution, under the condition of not affecting the clipping structure of conventional titanium clips, the circular step is arranged on the sleeve and is used together with the clip implanting device and the clip withdrawing device to link the titanium clip body and the sleeve, the titanium clip body can easily clip soft tissues by means of the first clip arms, and the clip implanting device can be disconnected and separated from the titanium clip body by means of the fragile portion under the action of an external force; moreover, when the titanium clip body in a human body needs to be detached, the second clip arms and the metal bar of the clip withdrawing device work together to quickly detach the titanium clip. In this way, the titanium clip can be implanted easily and detached directly by means of an endoscope, and secondary injuries to human bodies can be effectively avoided during the detachment process.

DETAILED DESCRIPTION OF THE INVENTION

To gain a better understanding of the objectives, technical solutions and advantages of the invention, the invention will be described in further detail below in conjunction with accompanying drawings and embodiments. It should be understood that the specific embodiments described below are merely used for explaining the invention and are not used for limiting the invention.

In the description of the invention, it should be understood that terms such as "center", "longitudinal", "transverse", "length", "width", "thickness", "upper", "lower", "front", "back", "left", "right", "vertical", "horizontal", "top", "bottom", "inner", "outer", "clockwise" and "anticlockwise" are used for indicating directional or positional relations based on the accompanying drawings merely for the purpose of facilitating and simplifying the description of the invention, do not indicate or imply that devices or elements referred to must be in a specific direction or configured and operated in a specific direction, and thus should not be construed as limitations of the invention. In addition, terms "first" and "second" are merely for the purpose of description, and should not be construed as indicating or implying relative importance or implicitly indicating the number of technical features referred to. Therefore, a feature defined by "first" or second" may explicitly or implicitly indicate the inclusion of one or more said features. In the description of the invention, "multiple" means two or more, unless otherwise clearly and expressly defined.

In the description of the invention, it should be noted that, unless otherwise expressly stated and defined, terms "mount", "join" and "connect" should be broadly understood. For example, "connect" may refer to fixed connection, detachable connection or integrated connection; or, mechanical connection or electrical connection; or, direct connection, or indirect connection by means of an intermediate medium, or internal connection or interaction of two elements. Those ordinarily skilled in the art can appreciate the specific meanings of these terms in the invention as the case may be.

Figure 1:
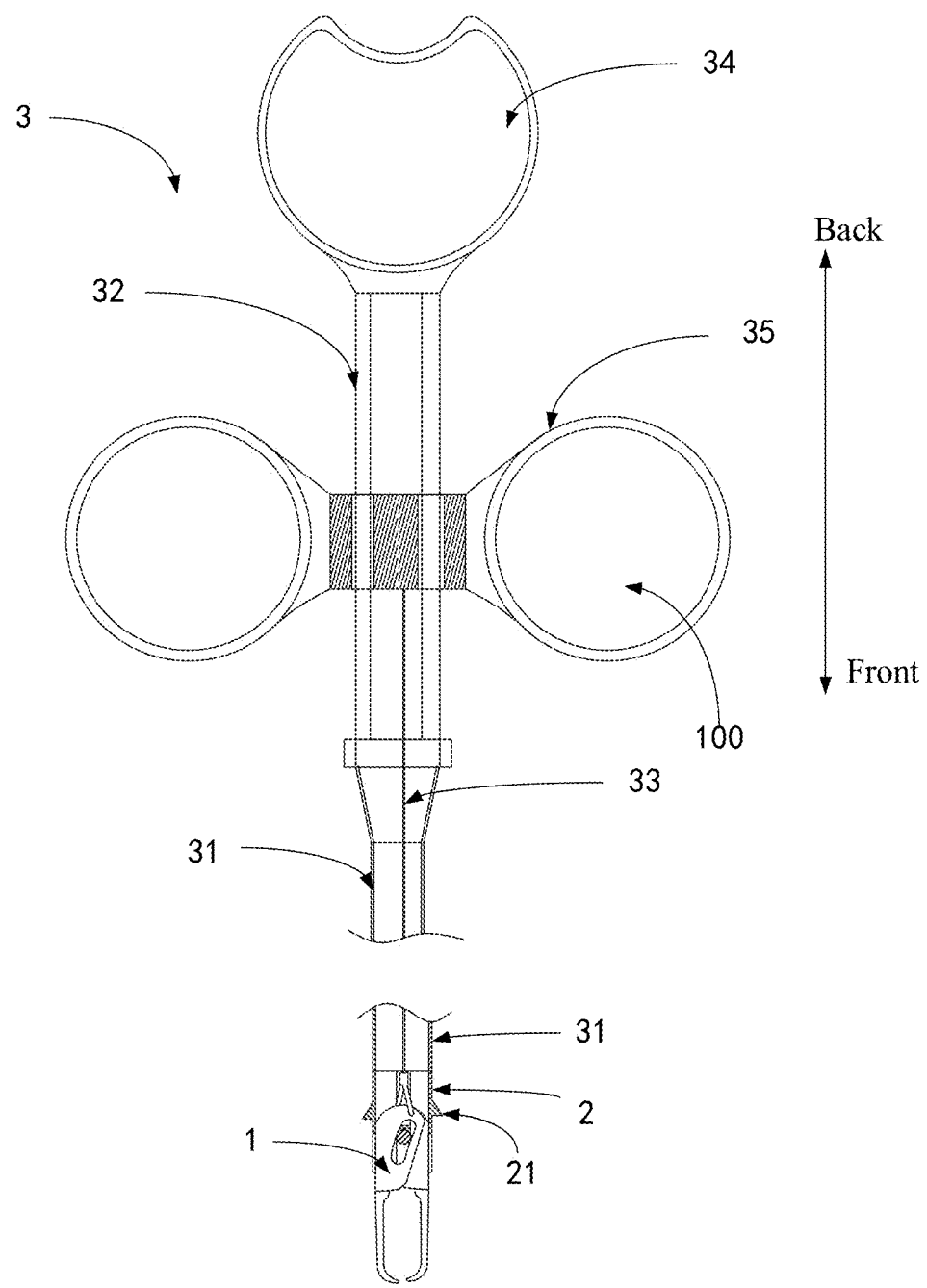
FIG. 1 is a schematic structural diagram according to one embodiment of the invention.
Figure 2:
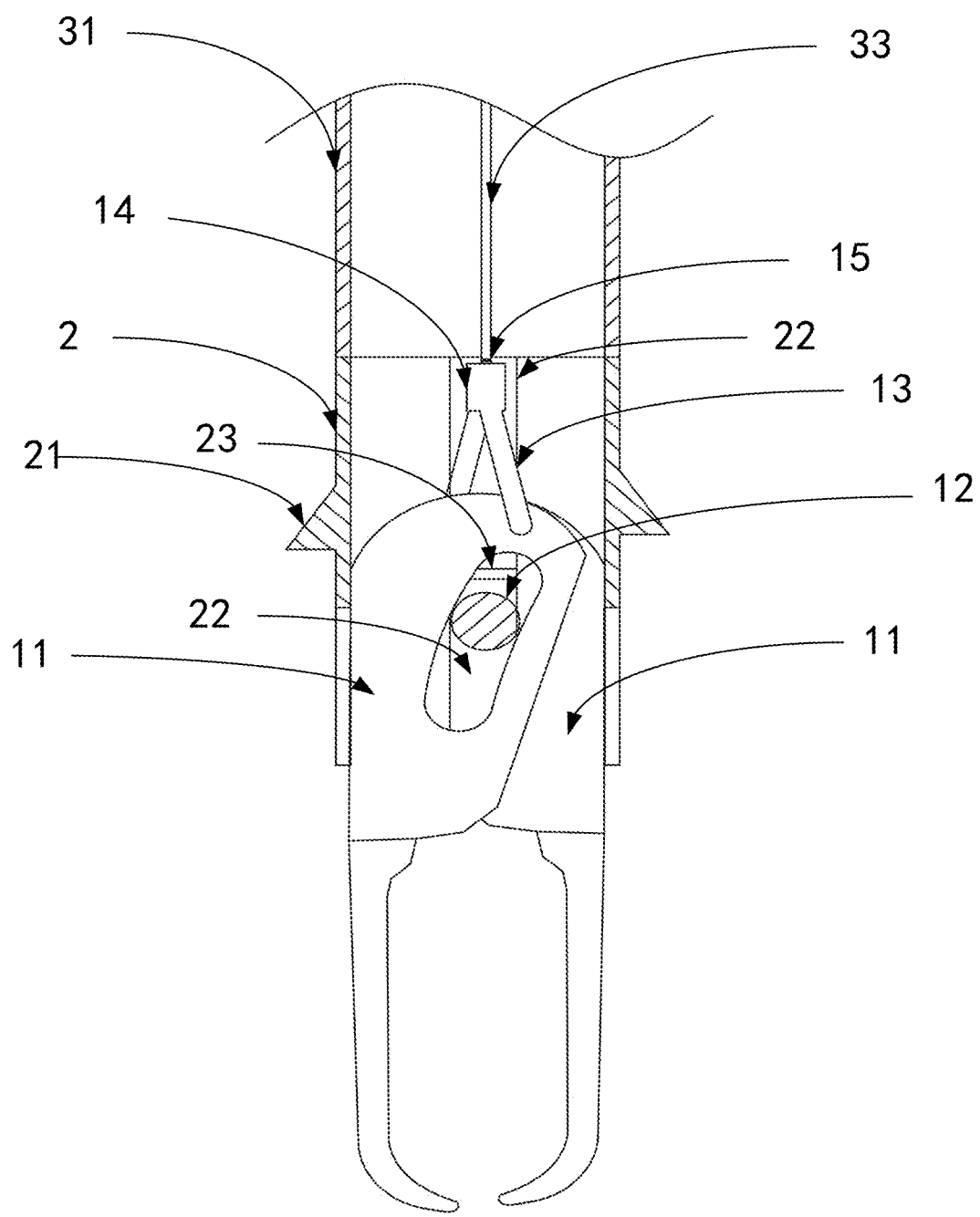
FIG. 2 is a schematic structural diagram when a titanium clip body and a clip implanting device are used together according to one embodiment of the invention.
Figure 3:
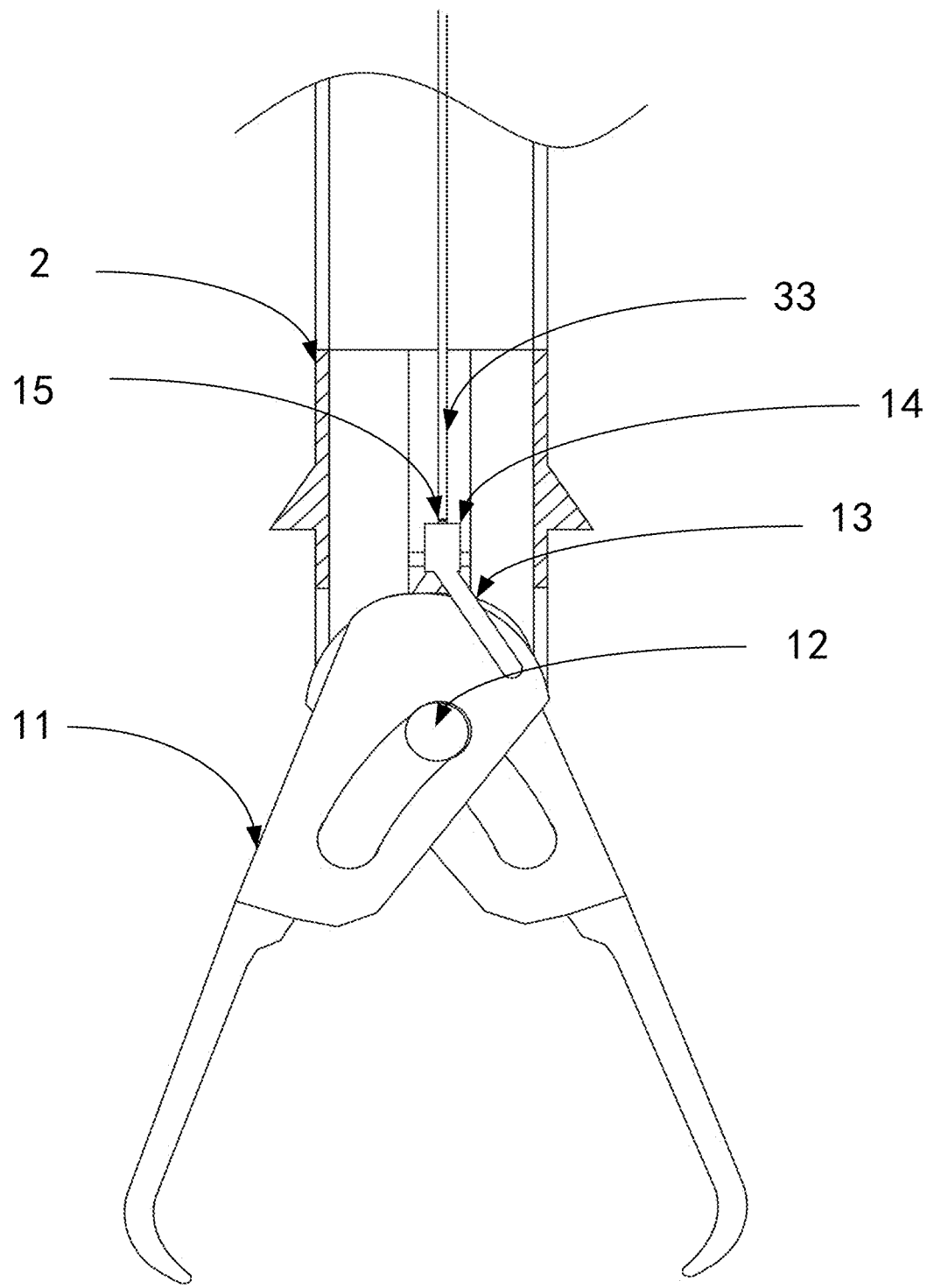
FIG. 3 is a schematic structural diagram of the titanium clip body in an open state according to one embodiment of the invention.
Figure 4:
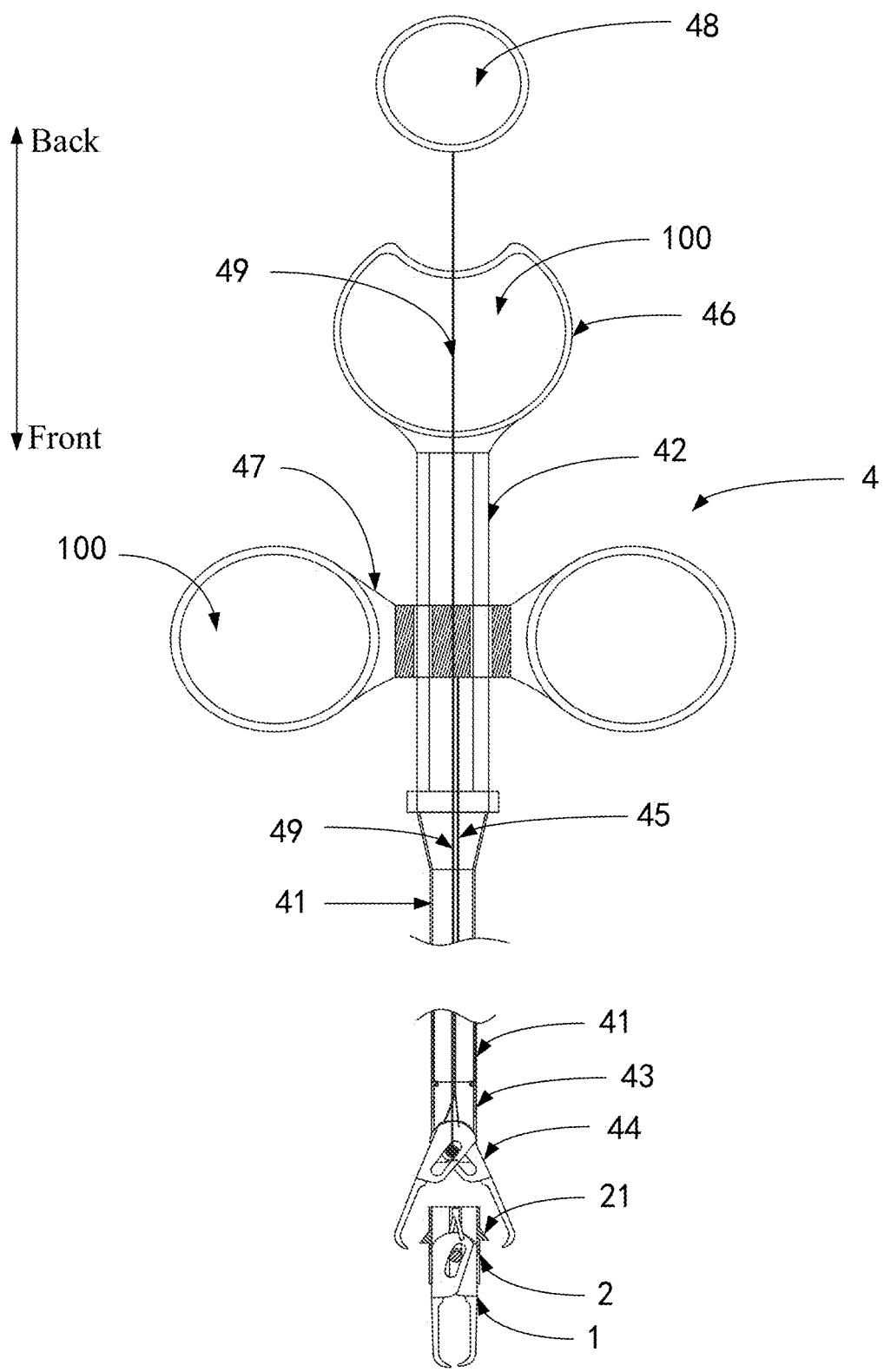
FIG. 4 is a schematic structural diagram when the titanium clip body and a clip withdrawing device are used together according to one embodiment of the invention.
Figure 5:
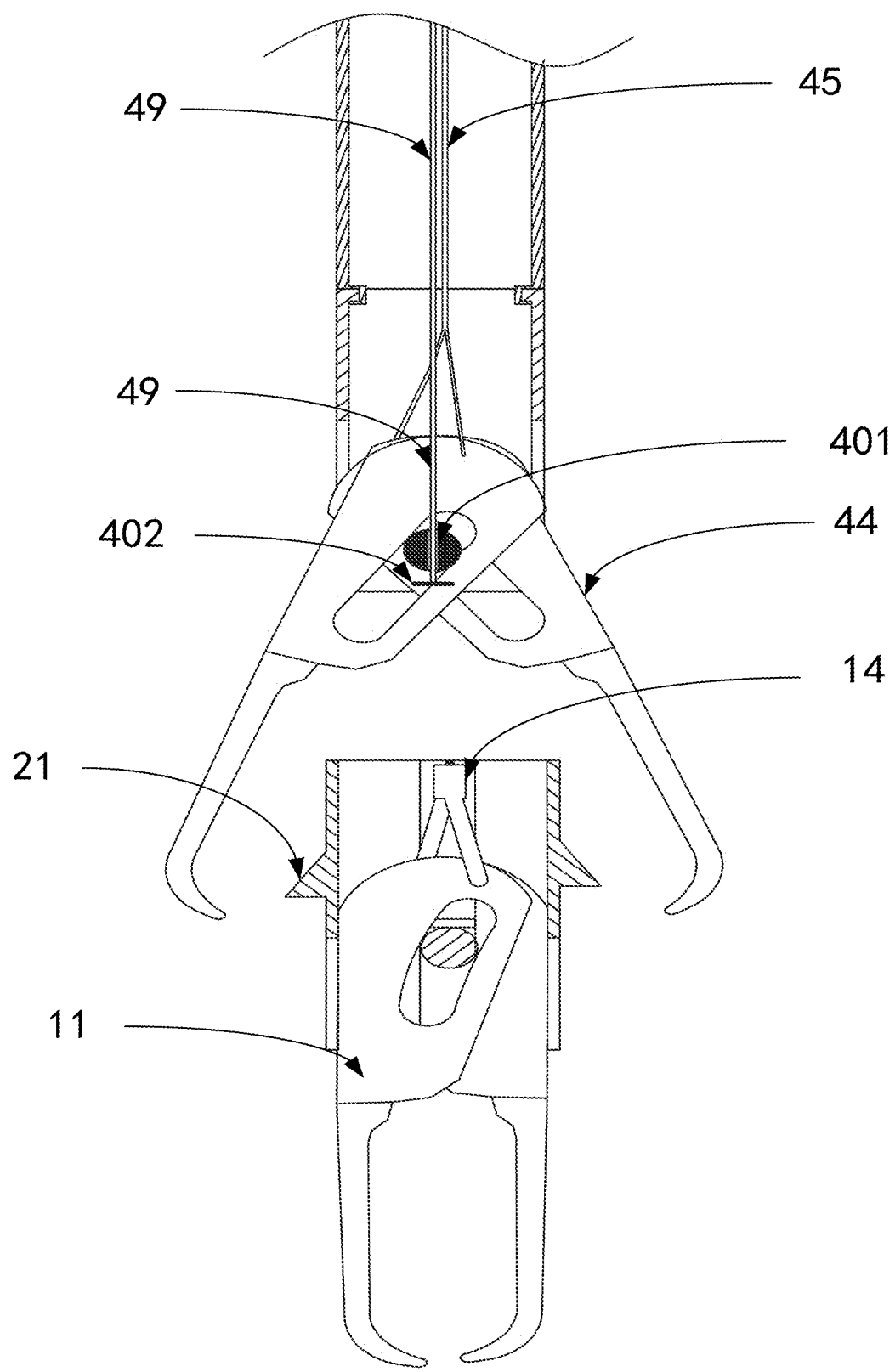
FIG. 5 is a schematic structural diagram when the titanium clip body and a clip withdrawing sheath are used together for detachment according to one embodiment of the invention.

As shown in FIG. 1 to FIG. 5, this embodiment provides a detachable titanium clip assembly, comprising:

a titanium clip body 1, wherein the titanium clip body 1 comprises two first clip arms 11, a hinge bar 12 is arranged between the first clip arms 11, the first clip arms 11 are allowed to move along the hinge bar 12 to be opened or closed, one ends of elastically deformable connecting rods 13 are arranged at tails of the first clip arms 11, the other ends of the connecting rods 13 are integrated to form a connecting end 14, and a fragile portion 15 to be snapped under an external force is arranged at the connecting end 1; or, the connecting rods 13 are rigid, and the two ends of each of the connecting rods 13 are respectively connected to the tail of the corresponding first clip arm 11 and the connecting end 14 in a hinged manner;

a sleeve 2, wherein the sleeve 2 is cylindrical and disposed around the titanium clip body 1, the first clip arms 11 of the titanium clip body 1 are forced to be closed by pushing the sleeve 2 on the titanium clip body 1, a circular step 21 protruding outwards is arranged on a side face of the sleeve 2, sliding grooves 22 are formed in an inner wall of the sleeve 2, and two ends of the hinge bar 13 are arranged in the sliding grooves 22; wherein, limiting portions 23 for preventing the titanium clip body 1 from being further pulled upwards are arranged at top ends of the sliding grooves 22 or in the sleeve 2;

a clip implanting device 3, wherein the clip implanting device 3 comprises a clip implanting sheath 31 and a clip implanting handle 32, an end of the clip implanting sheath 31 abuts against the sleeve 2, a first pull wire 33 is arranged in the clip implanting sheath 31, a first clipping portion 34 to be held or gripped by fingers is arranged on the clip implanting handle 32, a first moving portion 35 to be held or gripped by fingers is disposed around the clip implanting handle 32, one end of the first pull wire 33 is connected to the first moving portion 35, the other end of the first pull wire 33 is connected to the fragile portion 15, and the first moving portion 35 is vertically pushable with respect to the clip implanting handle 32 to drive the titanium clip body 1 to move vertically in the sleeve 2; and a clip withdrawing device 4, wherein the clip withdrawing device 4 comprises a clip withdrawing sheath 41 and a clip withdrawing handle 42, a rotary sleeve 43 is rotatably mounted at one end of the clip withdrawing sheath 41, the other end of the clip withdrawing sheath 41 is connected to the clip withdrawing handle 42, the rotary sleeve 43 is hinged and connected to two second clip arms 44 used for clipping, one end of each of the second clip arms 44 is formed with a jaw and located outside the rotary sleeve 43, the other end of each of the second clip arms 44 is connected to a second pull wire 45, a second clipping portion 46 to be held or gripped by fingers is arranged on the clip withdrawing handle 42, a second moving portion 47 to be held or gripped by fingers is disposed around the clip withdrawing handle 42, the second pull wire 45 is connected to the second moving portion 47, the second moving portion 47 is vertically pushable with respect to the clip withdrawing handle 42, a push ring 48 is arranged on the clip withdrawing handle 42 and connected to a metal bar 49, receding holes 401 are formed in positions, corresponding to the metal bar 19, of the second clip arms 44, the metal bar 49 penetrates through the clip withdrawing handle 42 to be arranged in the clip withdrawing sheath 41 and abuts against the connecting end 14 of the titanium clip body 1 after being pushed forwards by the push ring 48, and the second clip arms 44 are able to clip the circular step 21 on the sleeve 2 to prevent the sleeve 2 from moving.

In this embodiment, under the condition of not affecting the clipping structure of conventional titanium clips, the circular step 21 is arranged on the sleeve 2 and is used together with the clip implanting device 3 and the clip withdrawing device 4 to link the titanium clip body 1 and the sleeve 2, the titanium clip body 1 can easily clip soft tissues by means of the first clip arms 11, and the clip implanting device 3 can be disconnected and separated from the titanium clip body 1 by means of the fragile portion 15 under the action of an external force; moreover, when the titanium clip body 1 in a human body needs to be detached, the second clip arms 44 and the metal bar 49 of the clip withdrawing device 4 work together to quickly detach the titanium clip. In this way, the titanium clip can be implanted easily and detached directly by means of an endoscope, and secondary injuries to human bodies can be effectively avoided during the detachment process.

Further, to allow the second clip arms 44 to better clip the sleeve 2, in this embodiment, the cross-section of the circular step 21 is frustum-shaped, and the area of the bottom of the circular step 21 is greater than the area of the top of the circular step 21, such that a horizontal surface is formed at the lower end of the circular step 21, and a sufficient clipping area and force can be provided; the circular step 21 is arranged around the sleeve 2, such that the second clip arms 44 can directly clip the circular step 21 during actual operation no matter in which direction the second clip arms 44 is; and the maximum diameter of the circular step 21 is less than 3.6 mm. Wherein, the circular step 21 may be replaced with a circular groove or a hollow groove. The circular groove may be a whole circular groove or be formed by three recesses, and the hollow groove may be formed by multiple hollow portions arranged in a circular shape.

Further, to ensure that the metal bar 49 can easily eject the titanium clip body 1, in this embodiment, a top surface of the connecting end 14 of the titanium clip body 1 is a flat surface, such that the metal bar 49 can be in contact with the connecting end 14 in a sufficient area, and slipping can be avoided when the metal bar 49 ejects the titanium clip body 1. In addition, a flat plate 402 is arranged at a top end of the metal bar 49, thus ensuring that the metal bar 49 can normally eject the titanium clip body 1 by means of the two flat surfaces. Wherein, the flat plate 402 may be a cone, the flat plate becomes thicker from a portion 15 mm away from the metal bar, can transfer a force and will not deform, and the flat plate 402 is located between the two second clip arms 44 when the second clip arms 44 are closed.

Further, to ensure that doctors can operate the titanium clip easily, in this embodiment, circular rings 100 allowing fingers to penetrate through are arranged on the first clipping portion 34, the first moving portion 35, the second clipping portion 46 and the second moving portion 47.

Further, in this embodiment, the clip implanting sheath 31 and the clip withdrawing sheath 41 are both flexible sheaths.

Further, to improve the clipping stability of the first clip arms 11 and the second clip arms 44, in this embodiment, hooks are arranged at mouths of the first clip arms 11 and the second clip arms 44 respectively. The hooks are used to clip soft tissues and the circular step 21, such that the soft tissue and the circular step 21 can be clipped more firmly. As for the specific shape of the hooks, the hooks are L-shaped or spoon-shaped. The specific structure of the hooks is not limited in this embodiment.

This embodiment further provides a use method of the detachable titanium clip assembly, specifically comprising the following steps:

S1, in a default state where the clip implanting device 3, the titanium clip body 1 and the sleeve 2 are assembled together and the titanium clip body 1 is in a closed state, the clip withdrawing device 3 is operated, and the first moving portion 35 of the clip withdrawing device 3 is kept static for later use;

S2, the clip implanting device 3 is inserted into a human body along a biopsy passage of an endoscope; when the clip implanting device 3 is pushed to a soft tissue, that is, the first clip arms 11 of the titanium clip body 1 reach the soft tissue, the clip implanting handle 32 of the clip implanting device 3 is operated to push the first moving portion 35 forwards to gradually push the first clip arms 11 out of the sleeve 2 to be opened, then the first clip arms 11 in the open state are pushed to the soft tissue, the first moving portion 35 is then pushed backwards to pull the connecting end 14 of the titanium clip body 1 by means of the first pull wire 33 such that the titanium clip body 1 is gradually pulled back into the sleeve 2, and in the process of gradually pulling the titanium clip body 1 back into the sleeve 2, the first clip arms 11 of the titanium clip body 1 are closed gradually until the soft tissue is clipped by the first clip arms 11;

S3, after the titanium clip body 1 clips the soft tissue, because the titanium clip body 1 will not be pulled by further pulling the first pull wire 23 under the action of the limiting portions 23, a greater force is applied to the first moving portion 35 to snap the fragile portion 15 of the first pull wire 33;

S4, after the first pull wire 33 is snapped, the clip implanting device 3 is disconnected from the titanium clip body 1 and the sleeve 2 and then taken out of the endoscope, and at this moment, the titanium clip body 1 still clips the soft tissue under the action of the sleeve 2;

S5, when the titanium clip body 1 needs to be detached, the endoscope is pushed to the titanium clip body 1, and then the clip withdrawing device 4 is inserted into the human body along the endoscope, wherein the push ring 44 is maintained at an outmost end and the metal bar 49 is maintained in the receding holes 401;

S6, the second clip arms 44 of the clip withdrawing device 4 are placed on the circular step 21 on the sleeve 2, then the second moving portion 47 is pushed forwards to drive the second clip arms 44 to be opened and abut against the circular step 21, then the second moving portion 47 is pushed reversely to drive the second clip arms 44 to clip the circular step 21, and then the second moving portion 47 is kept static; and S7, after the second clip arms 44 clip the circular step 21, the push ring 48 is pushed forwards with an external force to gradually push the metal bar 49 out of the receding holes 401 to abut against the connecting end 14 of the titanium clip body 1, then the push ring 48 is further pushed to push the titanium clip body 1 out of the sleeve 2 to release the soft tissue, and at this moment, the titanium clip body 1 and the sleeve 2 are taken out of the human body by means of the second clip arms 44 of the clip withdrawing device 4.

The above embodiments are merely preferred ones of the invention and are not intended to limit the patent scope of the invention. All equivalent structures or flow transformations made according to the contents in the specification and accompanying drawings of the invention, or direct or indirect applications to other related technical fields should also fall within the patent protection scope of the invention.

What is claimed is:

1. A detachable titanium clip assembly, comprising:
a titanium clip body, wherein the titanium clip body comprises two first clip arms, a hinge bar arranged between the first clip arms, a fragile portion to be snapped under an external force and elastically deformable connecting rods, the first clip arms are allowed to move along the hinge bar to be opened or closed, one ends of the elastically deformable connecting rods are arranged at tails of the first clip arms, the other ends of the connecting rods are integrated to form a connecting end, and the fragile portion to be snapped under an external force is arranged at the connecting end;
a sleeve, wherein the sleeve is cylindrical and disposed around the titanium clip body, the first clip arms of the titanium clip body are forced to be closed by pushing the sleeve on the titanium clip body, a circular step protruding outwards is arranged on a side face of the sleeve in the axial direction, sliding grooves are formed in an inner wall of the sleeve, and two ends of the hinge bar are arranged in the sliding grooves; wherein, limiting portions for preventing the titanium clip body from being further moved vertically are arranged at top ends of the sliding grooves or in the sleeve;
a clip implanting device, wherein the clip implanting device comprises a clip implanting sheath and a clip implanting handle, an end of the clip implanting sheath abuts against the sleeve, a first pull wire is arranged in the clip implanting sheath, a first clipping portion to be held or gripped by fingers is arranged on the clip implanting handle, a first moving portion to be held or gripped by fingers is disposed around the clip implanting handle, one end of the first pull wire is connected to the first moving portion, the other end of the first pull wire is connected to the fragile portion, and the first moving portion is vertically pushable with respect to the clip implanting handle to drive the titanium clip body to move vertically in the sleeve; and
a clip withdrawing device, wherein the clip withdrawing device comprises a clip withdrawing sheath and a clip withdrawing handle, a rotary sleeve is rotatably mounted at one end of the clip withdrawing sheath, the other end of the clip withdrawing sheath is connected to the clip withdrawing handle, the rotary sleeve is hinged and connected to two second clip arms used for clipping, one end of each of the second clip arms is formed with a jaw and located outside the rotary sleeve, the other end of each of the second clip arms is connected to a second pull wire, a second clipping portion to be held or gripped by fingers is arranged on the clip withdrawing handle, a second moving portion to be held or gripped by fingers is disposed around the clip withdrawing handle, the second pull wire is connected to the second moving portion, the second moving portion is vertically pushable with respect to the clip withdrawing handle, a push ring is arranged on the clip withdrawing handle and connected to a metal bar, receding holes are formed in positions, corresponding to the metal bar, of the second clip arms, the metal bar penetrates through the clip withdrawing handle to be arranged in the clip withdrawing sheath and abuts against the connecting end of the titanium clip body after being pushed forwards by the push ring, and the second clip arms are able to clip the circular step on the sleeve to prevent the sleeve from moving.

2. The detachable titanium clip assembly according to claim 1, wherein a cross-section of the circular step is frustum-shaped, an area of a bottom of the circular step is greater than an area of a top of the circular step, and a maximum diameter of the circular step is less than 3.6 mm.

3. The detachable titanium clip assembly according to claim 2, wherein a top surface of the connecting end of the titanium clip body is a flat surface.

4. The detachable titanium clip assembly according to claim 3, wherein circular rings allowing fingers to penetrate through are arranged on the first clipping portion, the first moving portion, the second clipping portion and the second moving portion.

5. The detachable titanium clip assembly according to claim 4, wherein the clip implanting sheath and the clip withdrawing sheath are both flexible sheaths.

6. The detachable titanium clip assembly according to claim 1, wherein hooks are arranged at mouths of the first clip arms and the second clip arms respectively.

7. The detachable titanium clip assembly according to claim 1, wherein a flat plate is arranged at a top end of the metal bar.

8. A use method of the detachable titanium clip assembly according to claim 1, comprising the following steps:
   S1, in a default state where the clip implanting device, the titanium clip body and the sleeve are assembled together and the titanium clip body is in a closed state, operating the clip withdrawing device, and keeping the first moving portion of the clip withdrawing device static for later use;
   S2, inserting the clip implanting device into a human body along an endoscope; when the clip implanting device is pushed to a soft tissue, that is, the first clip arms of the titanium clip body reach the soft tissue, operating the clip implanting handle of the clip implanting device to push the first moving portion forwards to gradually push the first clip arms out of the sleeve to be opened, then pushing the first clip arms in the open state to the soft tissue, then pushing the first moving portion backwards to pull the connecting end of the titanium clip body by means of the first pull wire such that the titanium clip body is gradually pulled back into the sleeve, and in the process of gradually pulling the titanium clip body back into the sleeve, gradually closing the first clip arms of the titanium clip body until the soft tissue is clipped by the first clip arms;
   S3, after the titanium clip body clips the soft tissue, because the titanium clip body will not be pulled by further pulling the first pull wire under the action of the limiting portions, applying a greater force to the first moving portion to snap the fragile portion of the first pull wire;
   S4, after the first pull wire is snapped, disconnecting the clip implanting device from the titanium clip body and the sleeve, then taking the clip implanting device out of the endoscope, and at this moment, still clipping the soft tissue by the titanium clip body under the action of the sleeve;
   S5, when the titanium clip body needs to be detached, pushing the endoscope to the titanium clip body, and then inserting the clip withdrawing device into the human body along the endoscope, wherein the push ring is maintained at an outmost end and the metal bar is maintained in the receding holes;
   S6, placing the second clip arms of the clip withdrawing device on the circular step on the sleeve, then pushing the second moving portion forwards to drive the second clip arms to be opened and abut against the circular step, then pushing the second moving portion reversely to drive the second clip arms to clip the circular step, and then keeping the second moving portion static; and
   S7, after the second clip arms clip the circular step, pushing the push ring forwards with an external force to gradually push the metal bar out of the receding holes to abut against the connecting end of the titanium clip body, then further pushing the push ring to push the titanium clip body out of the sleeve to release the soft tissue, and at this moment, taking the titanium clip body and the sleeve out of the human body by means of the second clip arms of the clip withdrawing device.

* * * * *